(12) United States Patent
Henning et al.

(10) Patent No.: US 12,721,983 B2
(45) Date of Patent: Sep. 1, 2026

(54) CARRIER ELEMENT FOR MICRO-NEEDLES, AND MICRO-NEEDLE ARRAY DEVICE

(71) Applicant: LTS Lohmann Therapie-Systeme AG, Andernach (DE)

(72) Inventors: Andreas Henning, Messstetten (DE); Sebastian Scherr, Neuhäusel (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 966 days.

(21) Appl. No.: 17/916,290

(22) PCT Filed: Mar. 16, 2021

(86) PCT No.: PCT/EP2021/056687
§ 371 (c)(1),
(2) Date: Sep. 30, 2022

(87) PCT Pub. No.: WO2021/197836
PCT Pub. Date: Oct. 7, 2021

(65) Prior Publication Data

US 2023/0146417 A1 May 11, 2023

(30) Foreign Application Priority Data

Apr. 2, 2020 (DE) ..................... 10 2020 109 157.5

(51) Int. Cl.
*A61M 37/00* (2006.01)

(52) U.S. Cl.
CPC ..... *A61M 37/0015* (2013.01); *A61M 2209/06* (2013.01); *A61M 2209/08* (2013.01)

(58) Field of Classification Search
CPC ...... A61M 2037/0053; A61M 37/0015; A61M 2037/0023
See application file for complete search history.

(56) References Cited

U.S. PATENT DOCUMENTS

| | | | | |
|---|---|---|---|---|
| 10,500,386 | B2 * | 12/2019 | Tamaru | A61M 37/0015 |
| 2008/0183144 | A1 | 7/2008 | Trautman et al. | |
| 2013/0338597 | A1 | 12/2013 | McAllister | |
| 2017/0106179 | A1 | 4/2017 | Yamada et al. | |
| 2017/0304604 | A1 | 10/2017 | Kato | |
| 2019/0134368 | A1 | 5/2019 | Nagai et al. | |
| 2019/0350840 | A1 | 11/2019 | Hori et al. | |

FOREIGN PATENT DOCUMENTS

| | | | |
|---|---|---|---|
| AU | 2012211391 | A1 | 8/2012 |
| CN | 106512199 | B | 3/2017 |
| CN | 109152914 | A | 1/2019 |

(Continued)

*Primary Examiner* — Deanna K Hall
(74) *Attorney, Agent, or Firm* — The Webb Law Firm

(57) ABSTRACT

A carrier element for micro-needles for forming a micro-needle array has a plate-like base element. Mounting elements for respectively connecting to a micro-needle of the micro-needle array are provided on a front side of the base element. Connecting elements are also provided, in particular on the front side of the mounting elements. The connecting elements are formed in such a way that they have an undercut in the longitudinal direction such that the needles are reliably connected to the mounting elements.

17 Claims, 5 Drawing Sheets

(56) References Cited

FOREIGN PATENT DOCUMENTS

| | | | |
|---|---|---|---|
| CN | 110478612 | A | 11/2019 |
| EP | 3028735 | A1 | 6/2016 |
| EP | 3409318 | A1 | 12/2018 |
| EP | 3459584 | A1 | 3/2019 |
| JP | 2012075855 | A | 4/2012 |
| JP | 2016067723 | A | 5/2016 |
| KR | 20170044049 | A | 4/2017 |
| WO | 2008008557 | A1 | 1/2008 |
| WO | 2014105458 | A1 | 7/2014 |
| WO | 2017208962 | A1 | 12/2017 |
| WO | 2019139827 | A1 | 7/2019 |
| WO | 2020037157 | A1 | 2/2020 |

* cited by examiner

CARRIER ELEMENT FOR MICRO-NEEDLES, AND MICRO-NEEDLE ARRAY DEVICE

CROSS-REFERENCE TO RELATED APPLICATIONS

This application is the United States national phase of International Application No. PCT/EP2021/056687 filed Mar. 16, 2021, and claims priority to German Patent Application No. 10 2020 109 157.5 filed Apr. 2, 2020, the disclosures of which are hereby incorporated by reference in their entirety.

BACKGROUND OF THE DISCLOSURE

Field of the Disclosure

The disclosure relates to a carrier element for microneedles for forming a microneedle array or a microneedle array device. The disclosure further relates to a microneedle array device.

Description of Related Art

Microneedles are used to deliver active ingredients directly into the skin, also known as transdermal delivery. For this purpose, the microneedles are just long enough to penetrate only the outer skin layers, but preferably not to reach nerves and blood vessels, thus leaving them unharmed. Nevertheless, microneedles create small holes in the upper skin layers, which significantly increases the absorption of active ingredients compared to a purely external application of active ingredients to the skin.

Microneedle arrays, which have a plurality of microneedles, for example attached to a carrier surface, can be used for short-term delivery or for long-term application. A preferred way of delivering the active ingredient from the microneedles into the skin is that areas of the microneedles containing active ingredient or the entire microneedle dissolve or detach and can thus be absorbed by the body through the skin. For this purpose, the microneedles are in particular, at least partially, made of water-soluble substances or materials, respectively. In addition to the direct delivery of active ingredients through the microneedles themselves, it is also possible for the microneedles to have pores or cavities or to be formed as hollow needles in order to enable active ingredient delivery to the skin in this way. Furthermore, microneedles can also be free of active ingredients. In this case, for example, the active ingredient can be applied externally to the outside of the microneedles, or a substance containing the active ingredient can be applied to the corresponding skin area only after the microneedles have been removed from the skin, in order to deliver active ingredients in this way using microneedles.

Microneedles can be made of ceramic, metal, or polymer, among other materials. Preferably, one or more active ingredient components are added to these materials, thus resulting in a formulation of the microneedles.

Previously known methods for manufacturing therapeutic or diagnostic microneedles or microneedle arrays, respectively, are not suitable or only suitable to a limited extent for manufacturing in sufficient quality and/or quantity.

A common method of manufacturing microneedles involves casting the microneedles or entire microneedle arrays, respectively, for example using casting molds such as dies made of silicone. In particular due to the hydrophobic properties between the casting mold and the formulation applied to it, which is usually liquid, numerous problems arise in such manufacturing methods.

Often, two or more liquids are used to manufacture a microneedle array. First, a first liquid or formulation provided with an active ingredient is dosed onto the dies, so that the indentations forming the microneedles are filled in part with the first liquid. After this first liquid has dried, a second liquid which typically contains no active ingredient, is dosed onto the die, so that on the one hand, the indentations are filled completely and a closed cover layer interconnecting the needles is made. Here, there is a problem that the two liquids mix with each other, since the second liquid has to dissolve the first liquid at least partly or that the first liquid must not yet have dried completely so as to ensure a combination of the two liquids. In particular, migrations of the active ingredient into the second or a lower layer may occur, so that the availability of active ingredient is reduced. Moreover, there is a substantial disadvantage that a long drying process is required.

For a transdermal application of the microneedles, the microneedle array is usually placed on the skin and the needles are applied by exerting a uniform pressure on the rear side of the microneedle array. In such a manual application, it is extremely difficult to exert a uniform and unidirectional force on all needles.

Further, mechanical applicators are known for applying microneedle arrays. With such applicators, the microneedle array has to be arranged on the applicator first, using an adhesive film. This is difficult as well and may cause damage to individual needles.

Moreover, packaging is a problem with microneedle arrays, since the microneedle arrays have to be packaged individually, typically in a sterile manner. This is typically done using a blister, i.e. an in particular transparent packaging film. In order to meet the requirements relative to sterility, it is necessary that the blister is welded or sealed. Sealing on an adhesive layer involves a lot of effort. In particular, not all adhesives are suitable for this.

From EP 3 459 584, a carrier element for microneedles for forming a microneedle array is known. Such a carrier element has a plate-shaped base element. Mounting elements are provided on a front side of the base element. Here, the front side of the base element is the side facing to the microneedles. The mounting elements are formed in truncated cone shape and have a front side on which the conical microneedle is arranged. For manufacturing the microneedle array, it is known from EP 3 459 584 to dose a first liquid provided with active ingredient into conical indentations of a die. Here, the volume of the fluid is chosen such that the individual frustoconical indentations that form the microneedles are not filled completely. In the next step, the carrier element is placed on the die such that the frustoconical mounting elements protrude into the indentations and a connection is made between a front side of the mounting elements and the material forming the microneedles. Although it is known from EP 3 459 548 to provide one or more indentations in the front side of the mounting elements, there still is a problem that individual microneedles are not reliably connected with the mounting elements of the carrier element.

SUMMARY OF THE DISCLOSURE

It is an object of the disclosure to provide a carrier element with which a better connection with the microneedles can be realized. It is another object of the disclosure, which is independent from the above object, to provide an improved microneedle array device.

The object is achieved with a carrier element and with a microneedle device as described herein.

The carrier element for micro-needles according to the disclosure for forming a microneedle array has a plate-like base element. Mounting elements are provided on a front side of the base element. The mounting elements each serve for connection with in particular one microneedle of the microneedle array. Thus, the front side of the base element is the side facing in the direction of the microneedles when the carrier element is connected with microneedles.

Each mounting element is provided with one connecting element. Such a connecting element is provided in particular at the front side of the mounting elements, but may also be provided at a side face of the mounting elements or at both a side face and the front side of the mounting elements. In order to realize a better connection of the microneedles with the mounting elements, the connecting elements are formed such, according to the invention, that they have an undercut in the longitudinal direction. Here, the longitudinal direction is the center line or the line of symmetry of individual mounting elements and microneedles. As an alternative, the longitudinal direction is the demolding direction, i.e. the direction or axis in which the carrier element is removed from a die together with the microneedles. Due to the undercut in the longitudinal direction, provided according to the invention, the material of the microneedles engages, at least partially, around or behind the mounting elements or a connecting element provided on the mounting elements. Due to such an undercut, a significantly better connection is realized. Since it is preferred that the mounting elements of the carrier element are set into the indentations of the die as long as the liquid previously dosed into the indentations has not cured yet or at least not completely, the liquid reaches the corresponding undercut regions in a simple manner.

The connecting elements may be protrusions or the connecting elements may have protrusions, where it is of course possible that a carrier element has different connecting elements and/or combinations of different connecting elements on different mounting elements. With connecting elements formed as protrusions, these extend in the longitudinal direction and, in a preferred embodiment, form an undercut. This is realized in particular by the cross section of the protrusions tapering in the longitudinal direction; i.e., starting from the microneedle, the protrusion tapers towards the front side of the base element, i.e. in particular in the longitudinal direction.

For the cross section to taper, the protrusions preferably comprise a groove. The same may be circumferential and thus be formed in particular annularly. In side view, it is thus particularly preferred that the protrusions are formed in a mushroom shape. The protrusions thus comprise a cylindrical web with an in particular round or polygonal cross section. The same is connected to an enlargement, such as a head.

In a further preferred embodiment, the connecting elements are formed as indentations, transversal bores or the like in the mounting elements. Providing indentations, transversal bores or the like that, at least in part, do not extend in the longitudinal direction already result in an undercut being formed. During manufacture, the at least still viscous material of the microneedles enters these indentations, transversal bores or the like. After curing, an in particular positive connection is made which is reliable due to the undercut.

Such connecting elements provided as indentations, transversal bores or the like may of course be combined with the above described connecting elements which are in particular configured as protrusions.

In another preferred embodiment, the connecting elements are at least partly or completely formed as channels extending into the mounting element. In particular, the channels are arranged such that they do not extend into the longitudinal direction, at least in part, or present an angle of ±0° with respect to the longitudinal direction. Here, it is particularly preferred that the cross section of the channels widens in the longitudinal direction to form an undercut. Starting from the front side of the mounting elements, such channels thus preferably extend towards the front side of the base element and have at least one enlargement of the cross section in this direction. Thereby, an undercut is realized by the material of the microneedles entering the channel.

This particular design of the channel with an enlargement of the cross section may also be combined with the above described alternative embodiments of connecting elements.

Preferably, the channel or another indentation in the mounting element has a volume that is larger than the volume of the liquid from which the microneedle is made that is typically received during manufacture. Thereby, it is possible to receive excess material and to realize a secure connection. If necessary, the channel can extend to the rear side of the base element, so that even an egress of liquid would be possible.

In a particularly preferred embodiment, the carrier element is at least partially made from a material that absorbs solvent. The material is thus suitable to absorb the solvent present in the liquid forming the microneedle. This is advantageous, since it is then possible to already insert the carrier element into the indentations of the die in a state in which the material forming the needle is still very liquid, because a curing of the material forming the needles is ensured due to the absorption of solvent by the carrier element. Specifically, the mounting elements of the carrier elements comprise such a material.

With channels that extend to the rear side of the base element and are thus open, there is a further advantage that solvent can escape in a simple manner.

Specifically, it is advantageous to provide a holder on a rear side of the base element of the carrier element. Here, the rear side of the base element is opposite the front side and is directed away from microneedles when these are present. Such a holder or such a fixing element allows for a simple accommodation of the carrier element by an applicator. The holder may be, for example, a substantially cylindrical, pin-shaped protrusion. The same may have a circumferential groove so as to e.g. cooperate with a latching connection on the applicator.

Further, it is preferred to provide a connecting surface in an edge region on the front side and/or the rear side of the base element. In particular, the connecting surface is an adhesive surface. A packaging element, in particular a packaging film, such as a blister, may be provided on the adhesive surface. Thereby, it is possible in a simple manner to package the microneedles, in particular in a sterile manner. Due to the connection of the packaging element with the carrier element, a simple removal is possible. Specifically, upon removal, the risk of damaging the microneedles is significantly reduced. The edge region is preferably formed to be circumferential, in particular frame shaped.

The disclosure further relates to a microneedle array comprising a carrier element, wherein the carrier element is configured as described above and is developed in an advantageous manner. A microneedle is provided or arranged at at least a part of the mounting elements, in particular at each mounting element. Thus, this invention relates to a microneedle array manufactured using the above described carrier element.

The disclosure further relates to a microneedle array device. Such a device comprises a carrier element having at least one plate-shaped base element and mounting elements provided at a front side of the base element, each for connection with a respective microneedle of the microneedle array. The above described connecting elements, in particular in a preferred embodiment, do not have to be provided, while it is particularly preferred according to the disclosure that such connecting elements are provided in particular in the above described embodiments. In a microneedle array device according to the disclosure, microneedles are connected with the mounting elements. Further, a packaging element is provided by which the microneedles are packaged in particular in a sterile manner. As described above with reference to the carrier element, the packaging element is preferably arranged in an edge region of the carrier element. Here, the connection is preferably established via a connecting surface provided on the front side and/or the rear side of the base element of the carrier element.

The packaging element may also be designed such that it comprises a recess. The recess serves to receive the carrier element, wherein, in a preferred embodiment, the recess is closed at least on one side, in particular with a packaging film. The film is preferably designed such that it can be peeled off. Preferably, a packaging film or the like is arranged on the side on which the microneedles are arranged. After removal of the packaging film, it is thus readily possible to push the carrier element out of the recess and to apply the needles, in particular immediately.

As an alternative or in addition, a packaging film may also be provided on the opposite side, i.e. in the region of the rear side of the carrier element. This is advantageous in particular if the carrier element has a holder for connection with an applicator. Such a packaging film, in particular also a peelable one, may then be removed, wherein the applicator may be connected with the holder immediately thereafter. Using the applicators, it is then possible to remove the applicator in the direction of the applicator. If a corresponding film is provided on both sides, it is likewise possible to remove the film provided on the side of the microneedles and to move the carrier element in this direction using the applicator and to apply the microneedles directly.

The carrier element of the microneedle device is preferably developed in an advantageous manner, as explained above.

For manufacturing a microneedle array device, it is preferred that a die is used which has a plurality of in particular conical indentations. The indentations serve to form the microneedles. In a first step, a liquid, in particular a liquid provided with an active ingredient, is dosed into the indentations of the die. Here, the indentations are filled only in part. Subsequent thereto, in particular before the liquid has dried completely, a carrier element according to the disclosure is set into the indentations of the die such that the mounting elements protrude into the indentations and a connection between the liquid and the mounting elements is established due to the connecting elements connected with the mounting elements. This is effected in particular in such a manner that the liquid connects with the connecting elements such that these are enclosed or engaged behind in part. Thus, an undercut is formed.

BRIEF DESCRIPTION OF THE DRAWINGS

In the following, the disclosure is described in more detail by means of a preferred embodiment with reference to the accompanying drawings.

In the drawings.

DESCRIPTION OF THE INVENTION

Figure 1:
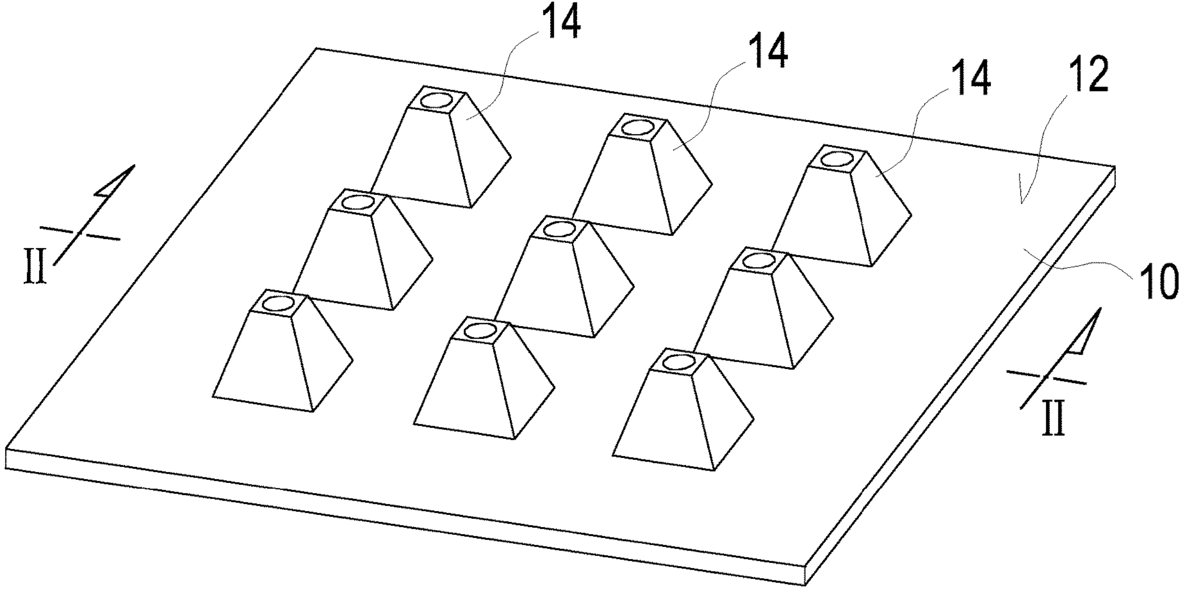
FIG. 1 is a schematic perspective view of a first embodiment of a carrier element from below.
Figure 2:
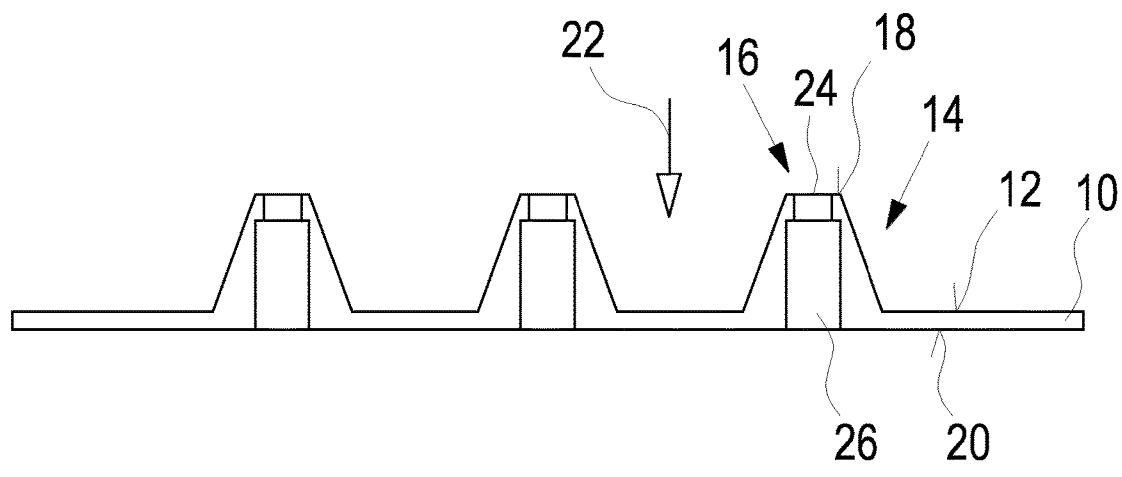
FIG. 2 is a schematic sectional view of the carrier element of FIG. 1 along line II-II.

A first embodiment of a carrier element (FIG. 1 and FIG. 2) comprises a plate-shaped base element 10. A plurality of frustoconical mounting elements 14 is arranged on a front side 12 of the base element 10. In the embodiment illustrated, only 9 such mounting elements are illustrated for the sake of clarity.

In the embodiment illustrated, each of the mounting elements 14 comprises a connecting element 16. In the first embodiment, the connecting element 16 designed as a channel that extends from a front side 18 of the mounting elements to a rear side 20 of the base elements. In a first section 24 of the channel 16 that extends in the longitudinal direction 22, the channel has a smaller diameter than in a second section 26. Due to the different cross sections in the sections 24 and 26 of the channel 16, an undercut is formed.

A die 28 (FIG. 3) is used to manufacture the microneedle array. The die 28 has a plurality of conical indentations 30. The arrangement and the number of the conical indentations 30 corresponds to the arrangement and the number of the mounting elements 14.

First, the indentations 30 are filled in part with a liquid 32. Here, the liquid 32, which contains an active ingredient, is dosed such that the indentations 30 are filled only in part.

Figure 4:
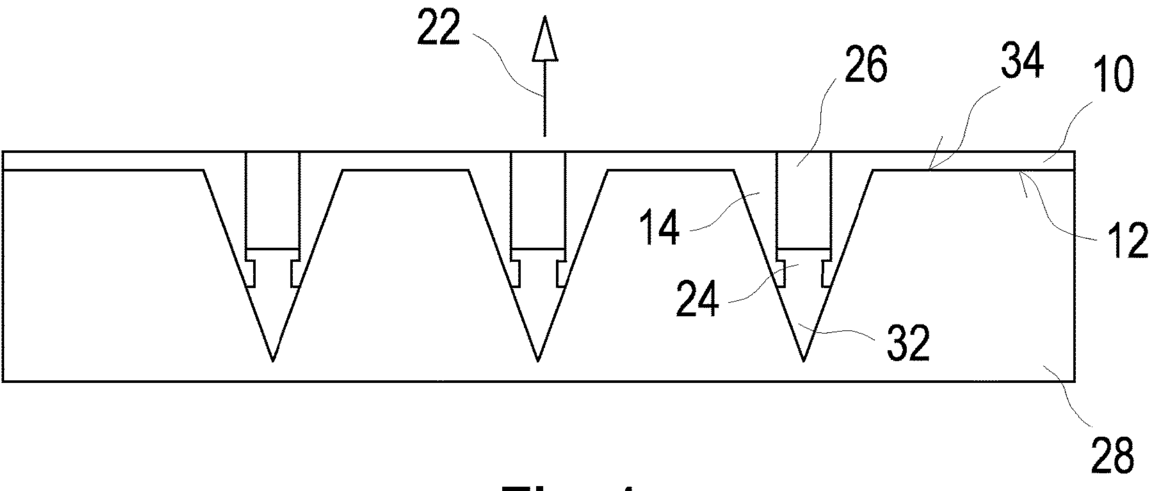
FIG. 4 is a schematic sectional view of the carrier element of FIGS. 1 and 2 in combination with the die of FIG. 3.

In the next step, the carrier material is placed on an upper surface 34 of the die 32 such that the front side 12 of the base element 10 rests on the upper surface 34 (see FIG. 4). Here, the mounting elements 14 are arranged in the indentations 30, with the liquid 32 penetrating into the channel 16, in particular into the first channel section 24. A part of the liquid also penetrates into the channel section 26 so that an undercut is made (as can be seen in FIG. 4). When demolding the carrier element in the longitudinal direction or the demolding direction 22, it is thus ensured that the parts 22 of the liquid forming the microneedles remain fixedly connected with the mounting elements 14 due to the undercut.

In the second embodiment described with reference to FIGS. 5 to 7, similar and identical components are identified by the same reference numerals.

In the second preferred embodiment, connecting elements 36 are provided as connecting elements on the front sides 18 of the mounting elements 14. The connecting elements 36 are designed as protrusions that are mushroom-shaped in cross section. Thus, the protrusions 36 have an in particular annular groove 38 in the longitudinal or demolding direction 22. The groove 38 forms an undercut with respect to a head-shaped element 40 of the protrusions 36.

Figure 3:
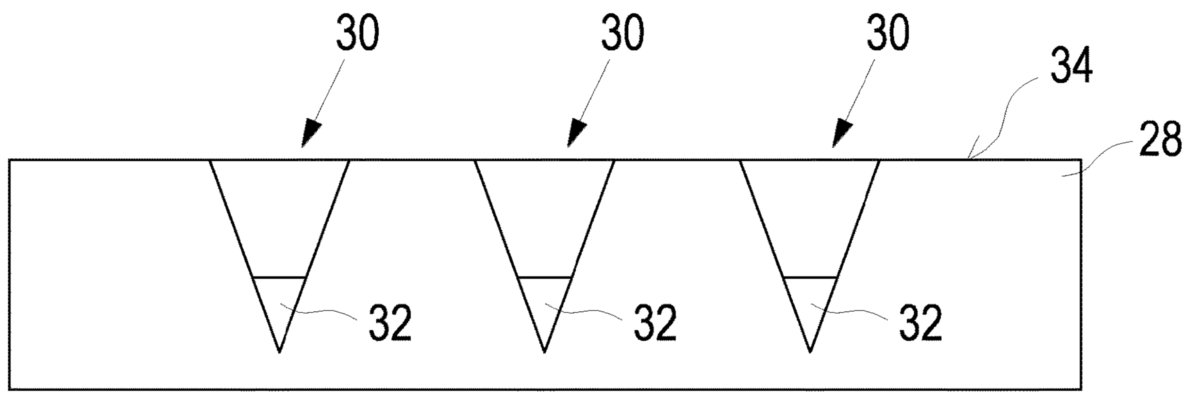
FIG. 3 is a schematic sectional view of a die.

The manufacture of a carrier element with microneedles is carried out correspondingly as described above with reference to the first embodiment and FIGS. 3 and 4. As can be seen in FIG. 7, the liquid 32 encloses the protrusions 36, so that, due to the undercut, firm, in particular positive connection between the mounting elements 14 and the liquid 32 forming the needle is realized.

Figure 5:
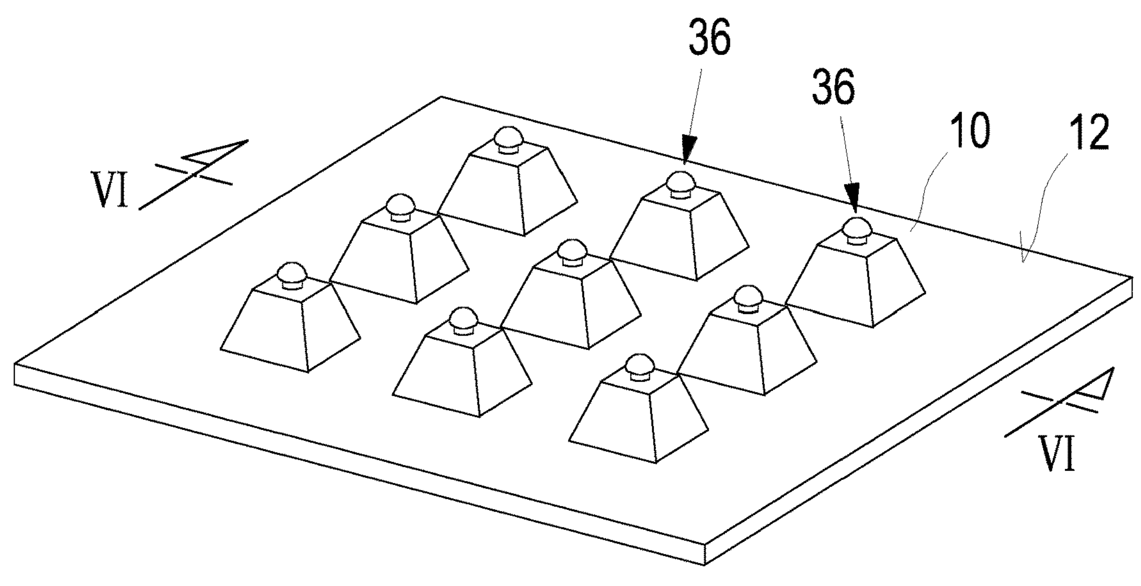
FIG. 5 is a schematic perspective view of a second embodiment of a carrier element from below.
Figure 6:
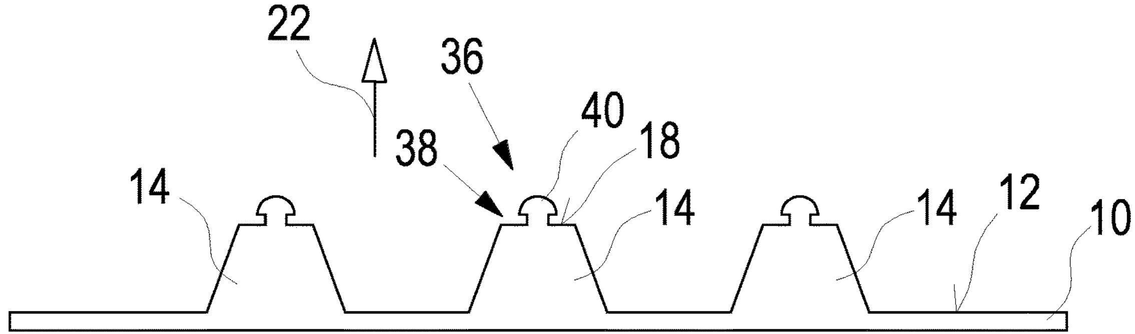
FIG. 6 is a schematic sectional view of the carrier element of FIG. 5 along line VI-VI.
Figure 7:
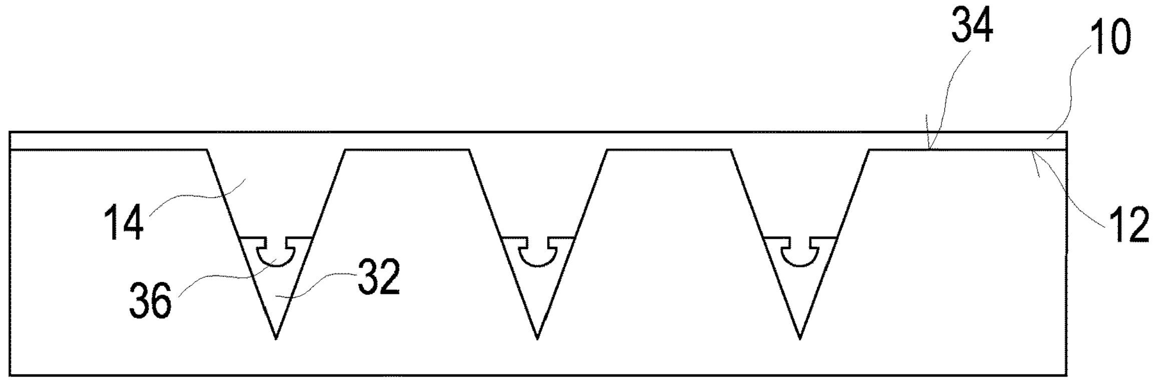
FIG. 7 is a schematic sectional view of the carrier element of FIGS. 5 and 6 in combination with the die of FIG. 3.
Figures 8, 9, 10:
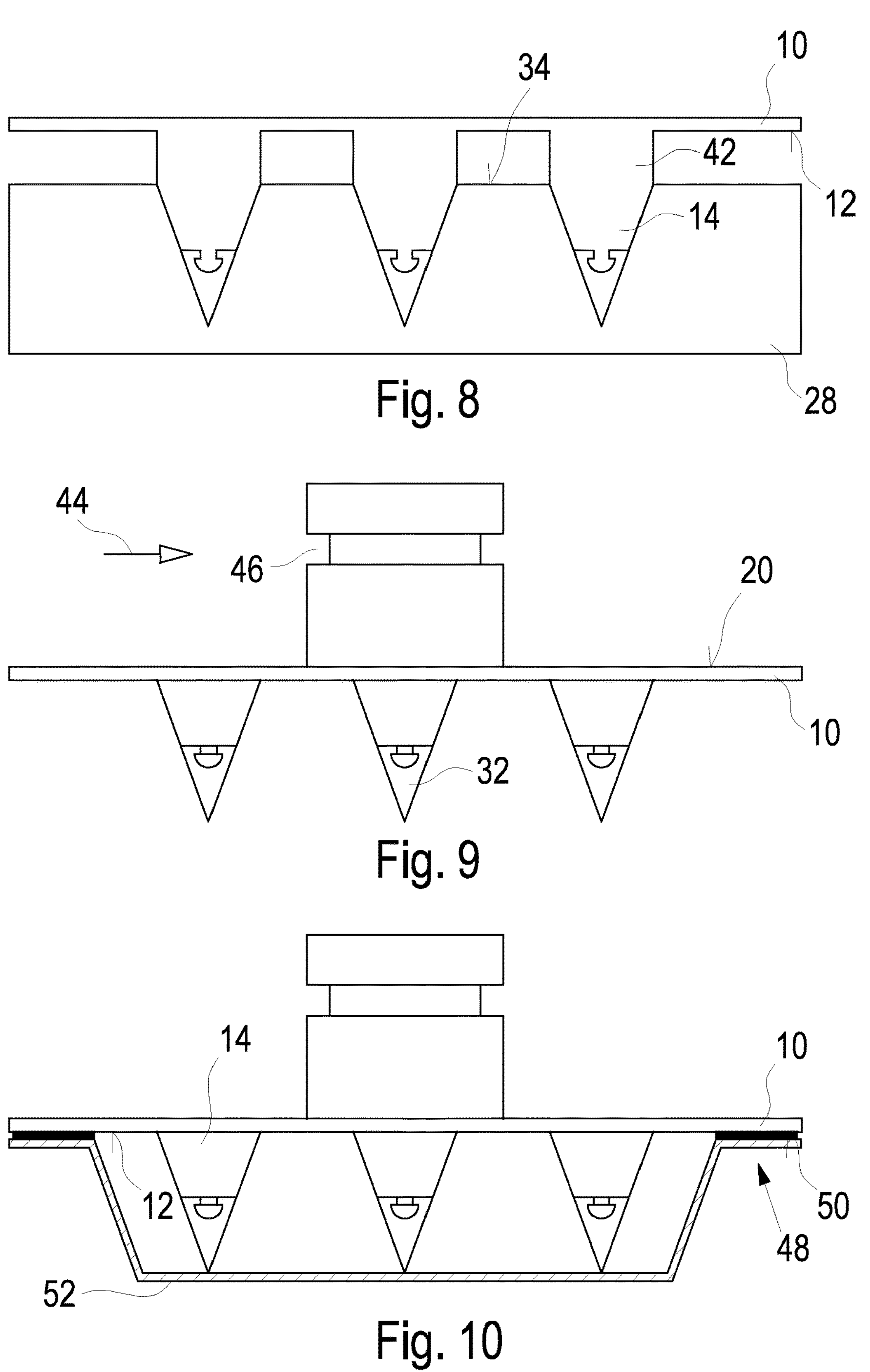
FIG. 8 is a schematic sectional view of the carrier element of FIGS. 5 and 6 according to an alternative embodiment.
FIG. 9 is a schematic side view of a further embodiment of the carrier element.
FIG. 10 shows a first preferred embodiment of a microneedle array device based on the carrier element of FIG. 9.

FIG. 8 illustrates an alternative embodiment to the embodiment illustrated in FIGS. 5 to 7. The connecting elements are designed identically. The only difference is that the mounting elements 14 comprise a longer shaft 42, so that the front side 12 of the base element 10 is spaced from the upper surface 34 of the die 28. Thereby, needles of different lengths can be manufactured in a simple manner, while using the same die 28.

FIG. 9 illustrates a development of the second embodiment illustrated in FIGS. 5 to 7. Here, a holder 34 is provided on the rear side 20 of the base element 10. In the embodiment illustrated, the holder 44 is formed to be circular cylindrical and has an annular groove 46. It is possible to connect the carrier element with an applicator via the holder 44. For example, a reliable fixation can be made by a latching connection that latches into the groove 46.

The holder 44 could of course also be arranged on the rear side of the first embodiment illustrated in FIGS. 1 to 4.

Figure 11:
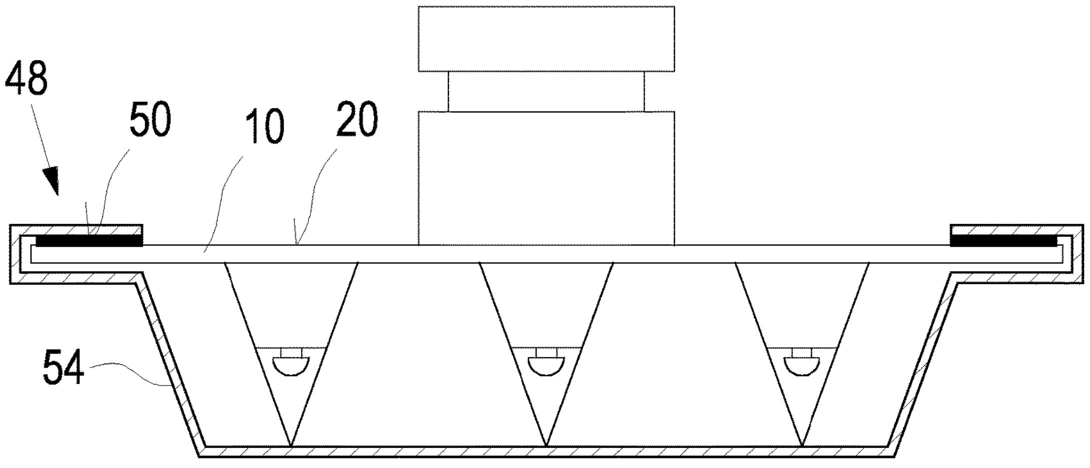
FIG. 11 shows a second preferred embodiment of a microneedle array device based on the carrier element of FIG. 9.
Figure 12:
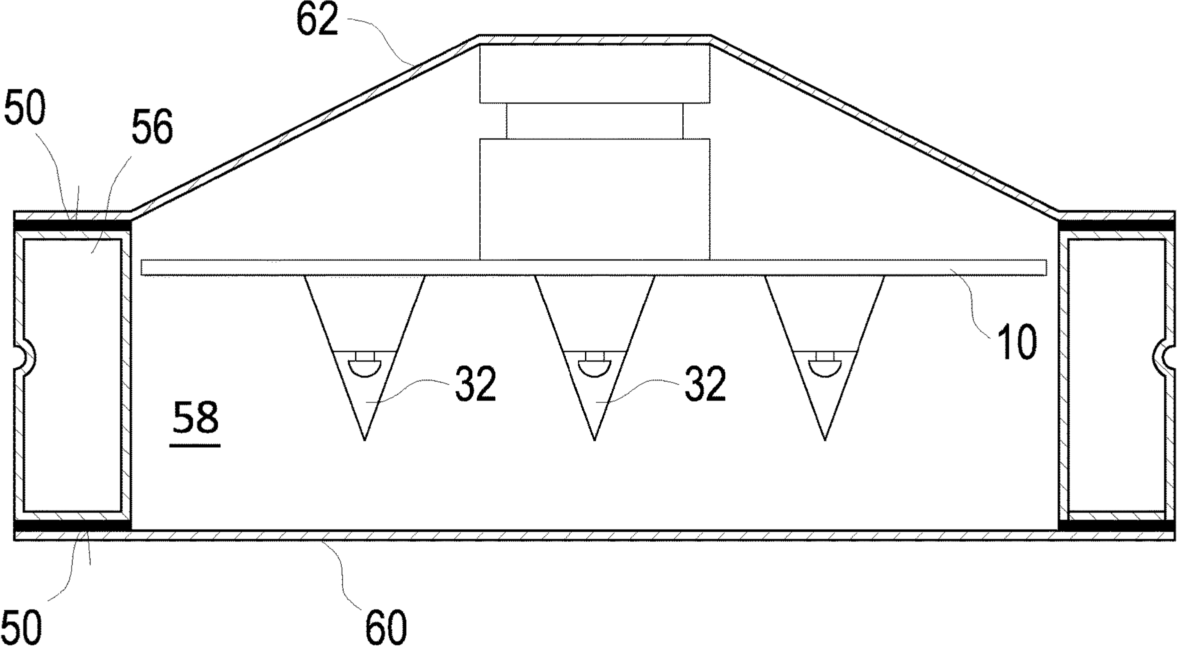
FIG. 12 shows a third preferred embodiment of a microneedle array device based on the carrier element of FIG. 9.

FIGS. 10 to 12 show different embodiments of a microneedle array device based on the carrier element with the holder 44 illustrated in FIG. 9.

For sterile packaging, the embodiment illustrated in FIG. 10 is provided with a connecting surface 50 in an edge region 48 on the front side 12 of the base element 10. In particular, the connecting surface 50 is an adhesive surface. The connecting surface 50 is provided circumferentially on the front side 12 of the base element 10 and thus encloses the mounting elements 14 in a frame-shaped manner. Using a packaging film 52 provided on the adhesive surface 50, it is readily possible to package the microneedle array, i.e. in particular the region that comes into contact with the patient, in a sterile manner.

An alternative packaging option is illustrated in FIG. 11. In this embodiment, the corresponding packaging element 54, which is again implemented in particular as a film, extends around the edge region of the base element 10. On the rear side 20, the connecting layer 50 is again provided in the edge region 48. This connecting layer is also formed in particular frame-shaped and encloses the entire base element 10.

In the embodiment illustrated in FIG. 12, the carrier element is arranged in an additional package 46 together with the needles 32 formed by the liquid. The additional package 56 has a recess or opening 58 in which in particular the base element 10 of the carrier element is arranged. In the embodiment illustrated, the recess is closed on the side of the microneedles 32 by a packaging film 60 which is fastened on the outer side of the additional package by adhesive surfaces 50. Opposite thereto, another packaging film 62 is provided which has an adhesive surface 50 on an outer side of the additional package 56.

The additional package illustrated in FIG. 12 provides protection for the entire carrier element including the holder 40 arranged on the rear side 20 of the base element 10. Here, the carrier element itself can be retained in the opening 58 of the additional package 56 by locking hooks, mounting elements or the like. Thereby, it is possible to readily retain the carrier element in a defined position until, for example, a force is applied by an applicator via the holder 44.

In the embodiment illustrated, a groove with a semicircular cross section may be provided in the outer side of the package 56. Thereby, it is possible to mount the entire additional package 56 in an applicator or receive it in an applicator. Then, all that is required for application is to remove the packaging film 60.

What is claimed is:

1. A carrier element for microneedles for forming a microneedle array comprising:

a plate-shaped base element;

mounting elements provided on a front side of the base element, each for connecting to one microneedle of the microneedle array; and connecting elements provided on the front sides of the mounting elements, wherein the connecting elements have an undercut in the longitudinal direction, wherein the connecting elements comprise, at least in part, protrusions extending in the longitudinal direction, and wherein the protrusions comprise a circumferential groove for forming a cross section taper.

2. The carrier element for microneedles for forming a microneedle array according to claim 1, wherein the protrusions comprise a cross section taper transverse to the longitudinal direction for forming the undercut.

3. The carrier element for microneedles for forming a microneedle array according to claim 1, wherein the protrusions are formed in a mushroom shape.

4. The carrier element for microneedles for forming a microneedle array according to claim 1, wherein the connecting elements comprise, at least in part, one or a plurality of channels extending into the mounting element.

5. The carrier element for microneedles for forming a microneedle array according to claim 4, wherein the channels do, at least in part, not extend in the longitudinal direction.

6. The carrier element for microneedles for forming a microneedle array according to claim 4, wherein the channels present, at least in part, a cross section enlargement for forming an undercut.

7. The carrier element for microneedles for forming a microneedle array according to claim 4, wherein, starting from the front side of the mounting element, the channels extend, at least in part, towards the front side of the base element.

8. The carrier element for microneedles for forming a microneedle array according to claim 4, wherein the channels extend, at least in part, from the front side of the mounting elements towards the rear side of the base element.

9. The carrier element for microneedles for forming a microneedle array according to claim 1, wherein a holder for holding the carrier element by an applicator is provided on a rear side of the base element.

10. The carrier element for microneedles for forming a microneedle array according to claim 1, wherein a connecting surface is provided in an edge region on the front side and/or the rear side of the base element.

11. A microneedle array with a carrier element according to claim 1, wherein microneedles are provided at each mounting element.

12. A microneedle array device comprising:

a carrier element for microneedles for forming a microneedle array according to claim 1;

microneedles connected with the mounting elements; and a packaging element packaging at least the microneedles.

13. The microneedle array device according to claim 12, wherein a connecting surface is provided in an edge region on the front side and/or the rear side of the base element.

14. The microneedle array device according to claim 12, wherein the packaging element comprises a recess for receiving the carrier element, the recess being closed at least on one side with a packaging film.

15. The microneedle array device according to claim 14, wherein the packaging film is provided at least on the side of the microneedles.

16. The microneedle array device according to claim 14, wherein a holder for holding the carrier element by an applicator is provided on a rear side of the base element.

17. The microneedle array device according to claim 12, wherein a holder for holding the carrier element by an applicator is provided on a rear side of the base element.

* * * * *